(12) United States Patent  (10) Patent No.: US 9,067,064 B2
Jiang et al.  (45) Date of Patent: Jun. 30, 2015

(54) OPTIMIZATION PROCESS FOR VOLUMETRIC MODULATED ARC THERAPY

(75) Inventors: Steve B. Jiang, San Diego, CA (US); Chunhua Men, Chesterfield, MO (US); Xun Jia, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 318 days.

(21) Appl. No.: 13/695,015

(22) PCT Filed: Apr. 28, 2011

(86) PCT No.: PCT/US2011/034402
§ 371 (c)(1),
(2), (4) Date: Jan. 7, 2013

(87) PCT Pub. No.: WO2011/139863
PCT Pub. Date: Nov. 10, 2011

(65) Prior Publication Data
US 2013/0131428 A1  May 23, 2013

Related U.S. Application Data

(60) Provisional application No. 61/329,014, filed on Apr. 28, 2010.

(51) Int. Cl.
*A61N 5/10*  (2006.01)
(52) U.S. Cl.
CPC ............ *A61N 5/1031* (2013.01); *A61N 5/1042* (2013.01); *A61N 5/1047* (2013.01)
(58) Field of Classification Search
CPC .. A61N 5/1031; A61N 5/1042; A61N 5/1047

USPC ............................... 378/65; 250/492.1–492.3
See application file for complete search history.

(56) References Cited

U.S. PATENT DOCUMENTS

| 6,192,103 | B1 | 2/2001 | Wormington et al. | |
| 6,560,311 | B1 | 5/2003 | Shepard et al. | |
| 2004/0165696 | A1* | 8/2004 | Lee | 378/65 |
| 2006/0256915 | A1* | 11/2006 | Otto et al. | 378/65 |
| 2009/0252292 | A1* | 10/2009 | Simon et al. | 378/65 |
| 2010/0119032 | A1* | 5/2010 | Yan et al. | 378/4 |
| 2012/0076271 | A1* | 3/2012 | Yan et al. | 378/65 |

OTHER PUBLICATIONS

Otto ("Volumetric modulated arc therapy: IMRT in a single gantry arc" Medical Physics 35 (1), Jan. 2008, pp. 310-317).*
Romeijn, et al ("A column generation approach to radiation therapy treatment planning using aperture modulation," SIAM J. Optim. 15(3) pp. 838-862).*
Men, C. et al., Ultrafast treatment plan optimization for volumetric modulated arc therapy (VMAT), Med. Phys. 37 (11), Nov. 2010, pp. 5787-5791.
Noh, Y. C., Authorized Officer, Korean Intellectual Property Office, International Search Report for PCT Application No. PCT/US2011/034402, Jan. 6, 2012, 2 pages.

* cited by examiner

*Primary Examiner* — Michael Maskell
(74) *Attorney, Agent, or Firm* — Perkins Coie LLP (57) ABSTRACT

Systems, techniques, and processes are disclosed for implementing aperture-based optimization techniques. In one aspect, a method performed by an aperture-based radiation treatment system includes implementing a volumetric modulated arc therapy (VMAT) treatment plan by generating apertures at beam angles. Beam intensities of the generated apertures are determined, which can be used to control generation of a radiation dose in a radiation therapy.

20 Claims, 8 Drawing Sheets

OPTIMIZATION PROCESS FOR VOLUMETRIC MODULATED ARC THERAPY

CROSS REFERENCE TO RELATED APPLICATIONS

This patent application is a 35 U.S.C. 371 National Stage application of International Application No. PCT/US2011/034402, filed on Apr. 28, 2011, which claims the benefit of U.S. Provisional Patent Application No. 61/329,014, filed Apr. 28, 2010, entitled "VOLUMETRIC MODULATED ARC THERAPY (VMAT)," the entire contents of which are incorporated herein by reference.

BACKGROUND

This application relates to systems, devices, and processes that use aperture-based optimization techniques.

Volumetric modulated arc therapy (VMAT) is a radiation therapy treatment technique which aims to deliver highly conformal radiation treatment. In a VMAT treatment process, a treatment gantry rotates around the patient while a radiation beam dynamically changes its aperture shape and associated intensity. VMAT is becoming a major treatment modality for cancer radiotherapy. VMAT requires less treatment time and fewer monitor units (MU) than Intensity Modulated Radiation Therapy (IMRT) techniques. Moreover, VMAT has the ability to deliver a more conformal dose to targets and lower dose to organs at risk (OARs). However, a VMAT treatment plan may include the full 360° of beam directions for optimization, which may take several hours with heuristic-based methods to optimize a plan.

SUMMARY

Systems, processes, and apparatus are disclosed for implementing an aperture-based method for volumetric modulated arc therapy (VMAT) treatment plan optimization to determine high quality treatment plans.

In one aspect, a method for implementing a VMAT treatment plan includes generating apertures at beam angles and determining beam intensities of the generated apertures, which are used to control radiation dose generation in a radiation therapy.

Implementations can optionally include one or more of the following features. The method can determine the beam intensity for a given aperture generated based on beam intensities for previously generated apertures. The method can generate apertures and determine the beam intensities using an iterative process. The method can allow beam angles to be user defined and be uniformly spaced for a rotation. The method can generate apertures using a column generation method. The method can generate a given aperture with the minimal objective value. The method can determine the aperture shapes and beam intensities using a cost function to characterize a quality of the radiation therapy, which can include a level of the radiation dose. The method can minimize the difference between beam intensities at two neighboring beam angles. The method can generate apertures by incorporating constraints for radiation dose deliverability.

In another aspect, a system for radiation treatment using a VMAT includes a VMAT processing unit and a radiation therapy device. A VMAT processing unit is configured to perform operations that generate apertures at beam angles and determine beam intensity of the generated apertures. A radiation therapy device is configured to use the determined beam intensities of the generated apertures to control radiation dose generation in a radiation therapy.

Implementations can optionally include one or more of the following features. The system can include a VMAT processing unit that can include a central processing unit (CPU). The system can include a VMAT processing unit that can include a graphics processing unit (GPU). The system can include a VMAT processing unit that can be configured to determine the beam intensity for a given aperture generated based on beam intensities for previously generated apertures. The system can include a VMAT processing unit that can be configured to determine the aperture shapes and beam intensities using a cost function to characterize a level of the radiation dose. The system can include a VMAT processing unit that can be configured to determine the beam intensities by minimizing the difference between beam intensities at two neighboring beam angles. The system can include a VMAT processing unit that can be configured to generate a given aperture by incorporating constraints for radiation dose deliverability.

In another aspect, a non-transient computer-readable medium embodying a computer program product adapted to cause a system to perform radiation treatment operations using a VMAT includes generating apertures at beam angles and determining beam intensities of the generated apertures, which are used to control radiation dose generation in a radiation therapy.

Implementations can optionally include one or more of the following features. The non-transient computer-readable medium can perform operations to determine the beam intensity for a given aperture generated based on beam intensities for previously generated apertures. The non-transient computer-readable medium can perform operations to determine the aperture shapes and beam intensities using a cost function to characterize a level of the radiation dose. The non-transient computer-readable medium can perform operations to determine the beam intensities by minimizing the difference between beam intensities at two neighboring beam angles. The non-transient computer-readable medium can perform operations to generate a given aperture by incorporating constraints for radiation dose deliverability.

The subject matter described in this specification potentially can provide one or more of the following advantages. In one example, the described system can be used to implement an aperture-based VMAT optimization process to generate clinically deliverable treatment plans with high plan quality and computational efficiency. The described systems and processes can be used to successfully optimize a VMAT treatment plan very rapidly. For example, a VMAT treatment plan can be optimized using the described processes in 5~8 minutes on a current state of the art desktop computer with a CPU and in about 30 seconds with a GPU.

BRIEF DESCRIPTION OF THE DRAWINGS

Like reference symbols and designations in the various drawings indicate like elements.

DETAILED DESCRIPTION

In a VMAT treatment process, a precisely sculpted and desired 3D dose distribution can be attained by optimizing the beam aperture shape formed by a multi-leaf collimator (MLC) and the beam intensity at each gantry angle. The optimization problem can be very complicated due to the very large scale of the problem and hardware constraints imposed on neighboring beam apertures and intensities. Processes, apparatus and systems described in this document can be used to develop an efficient aperture-based method for VMAT treatment plan optimization.

The systems, processes, and apparatus described in this document can be used to implement an aperture-based VMAT treatment plan optimization process, e.g., an algorithmic method or algorithm, which can determine high quality treatment plans.

In one aspect of the optimization process, a VMAT optimization problem can be formulated as a large-scale convex programming problem. A column generation approach can be developed to deal with its huge dimensionality. An algorithm can be implemented to generate apertures one by one in a sequential way. At each iteration of the column generation method, a deliverable aperture can be generated for one of the unoccupied beam angles by solving a subproblem with the consideration of deliverability constraints imposed by the MLC system. A subsequent master problem can be solved to optimize the intensities, e.g., determine the dose rate, for all generated apertures. When all beam angles are occupied, the optimization may complete, which can yield a set of deliverable apertures and associated dose rates that produce a high quality plan. Alternatively, the optimization plan can continue to generate new apertures to replace existing ones, or can generate new apertures in addition to the existing ones to form additional arcs.

Optimization Model

The described optimization process can be applied to various types of optimization models, such as convex optimization models. In one aspect, the described optimization process can be applied to an exemplary optimization model developed for a VMAT treatment plan. In other aspects, the optimization process can be applied to other optimization models, such as a biologically based model.

In this exemplary optimization model for a VMAT treatment plan, the number of beams can be denoted by N, and these beams can be sorted based on the beam angles from 0° to 359°, for example. A beam aperture can be a snapshot of the MLC leaf positions at a point in time during the radiation dose delivery. Each beam aperture, $A_k$, can be decomposed into a set of beamlets and can denote the set of beamlets exposed in beam k at angle $\Theta_k$. A decision variable $y_k$ can be associated with beam k that indicates the intensity of that aperture. The set of voxels that represents the patient's CT image can be denoted by V. In addition, the dose to a voxel j can be denoted by $z_j$ (j ∈ V). $z_j$ (j ∈ V) can be calculated using a linear function of the intensities of the apertures through the dose deposition coefficients, $D_{ij}$, where $$z_j = \sum_{k=1}^{N} y_k \sum_{i \in A_k} D_{ij}.$$

$D_{ij}$ is the dose received by the voxel j ∈ V from the beamlet i ∈ $A_k$ at unit intensity. $D_{ij}$ can be calculated using a dose calculation engine implemented on a general purpose GPU.

The exemplary VMAT optimization model can employ an objective function that can include a cost function F(z). F(z) can be used to enforce a desired dose distribution with quadratic one-sided voxel-based penalties. The cost function for a voxel j ∈ V can be calculated as:

$$F(z) = \alpha_j (\max\{0, T_j - z_j\})^2 + \beta_j (\max\{0, z_j - T_j\})^2,$$

where $\alpha_j$ and $\beta_j$ represent the weights for underdosing and overdosing penalty, respectively. For target voxels, we can set $\alpha_j > 0$ and $\beta_j > 0$ to penalize any deviation from the prescription dose $T_j$. As for critical structures, $\alpha_j = 0$ and $\beta_j > 0$ can be chosen to add penalty for only those voxels that received a dose exceeding a threshold $T_j$.

In a VMAT system, the dose rate variation between neighboring angles can be constrained within a certain range. To ensure the plan deliverability regarding this constraint, a smoothing term G(y) can be added with the cost function in the exemplary VMAT optimization model to minimize the difference between beam intensities at two neighboring beam directions. The smoothing term can be formulated as $$G(y) = \sum_{k=1}^{N-1} \frac{(y_{k+1} - y_k)^2}{(\Theta_{k+1} - \Theta_k)}.$$

The exemplary VMAT optimization model can include an objective function that can be written as:

$$\min_{y, A_k} F(z) + \gamma G(y),$$

subject to:

$$z_j = \sum_{k=1}^{N} y_k \sum_{i \in A_k} D_{ij}$$

$y_k \geq 0$ k=1, 2, ..., N, where $\gamma > 0$ is a factor adjusting relative weights between the two terms. It is noted that $A_k$, the set of beamlets exposed in the aperture of beam k, is also a decision variable that can be optimized.

There can be more than one set of decision variables. For example, a first set of decision variables can include the MLC leaf positions (which decide the shape of aperture) in each beam direction, and the second set of decision variables can include the intensities of these selected apertures. The number of first decision variables (e.g., MLC leaf positions in each beam direction) can be huge (~$10^{20}$), while the number of second decision variables (e.g., intensities of selected apertures) can be quite limited (the number of apertures can be denoted by n, where n=360, for example, if one aperture in each beam direction and one full rotation are chosen; multiple rotations or arcs can be allowed). Therefore, a column generation method can be developed and used, which iteratively can solve a subproblem and a master problem in an efficient manner. The subproblem can provide the most promising aperture to add to a given pool of allowable apertures. The master problem can optimize the intensities of these selected apertures. After n iterations, the implemented algorithm can then generate an optimized VMAT treatment plan.

Optimization Algorithm

Since the VMAT optimization problem can be of extremely large dimensionality, it poses a computational difficulty. The VMAT optimization problem can be solved using a column generation method as described in this document. The column generation method can also be used to solve direct aperture optimization (DAO) problem for IMRT treatment planning. VMAT optimization problem can include constraints in addition to nonnegative beam intensity constraints and MLC hardware deliverability constraints, as in DAO problem. Such constraints can include (1) the maximum MLC leaf motion speed and (2) the maximum radiation dose rate variation. The first constraint (e.g., the maximum leaf motion speed) can be handled as a hard constraint, while the second constraint (e.g., the maximum radiation dose rate variation) can be formulated as a penalty-based soft constraint in the objective function.

In the exemplary VMAT treatment plan, a gantry rotation can be made into discrete beam angles, for example 180 discrete beam angles. For each beam angle, one MLC aperture may be allowed. A single gantry rotation can include a movement that covers 360° or a movement that forms an arc and covers less than 360°. Multiple rotations may also be allowed. A rotation can also be made into discrete, uniformly spaced beam angles, e.g., 180 beam angles. A rotation can also be made into beam angles defined by a user, such as control points.

In the exemplary column generation method, one deliverable aperture can be generated at each beam angle, and the column generation method can find out the associated beam intensity. Apertures can be generated one by one in a sequential way. The optimization process can begin without any initial apertures. At each iteration, by solving a subproblem (also called a pricing problem), a new aperture can be generated for a beam angle that is not occupied by another aperture generated in previous iterations. It is noted that this beam angle can be automatically selected out of all unoccupied angles while solving the subproblem. The subproblem can identify an aperture which decreases the objective value most when added to the master problem. Moreover, generating a new aperture in this subproblem can account for all the deliverability constraints imposed by the MLC system. After the new aperture is generated, a master problem can be followed to find the optimal intensities associated with apertures already generated by minimizing the objective function. This iteration can terminate when every beam angle has been assigned one aperture.

The exemplary column generation method can be conducted as follows. For the subproblem, by checking the Karush-Kuhn-Tucker (KKT) conditions, the "price" $w_i$ for each beamlet i can first be obtained. The KKT conditions can be sufficient for a solution to be optimal in nonlinear convex programming. The "price" of a beamlet can characterize the degree that the objective value can be lowered if this beamlet is included in the aperture. The objective value measures the quality of the treatment plan. For example, the smaller the objective value in a VMAT treatment plan, the better the quality of the VMAT treatment plan. The quality of the treatment plan can include a level of radiation dose in a radiation therapy. The goal at this step in the subproblem can be to find a set of beamlets to form a deliverable aperture at one of the un-occupied beam angles that has the lowest total "price", i.e., the most effective reduction of the objective function. The set of all deliverable apertures in those un-occupied beam angles can be denoted by $K_U$, and the subproblem then can become:

$$\min_{A_k \in K_U} \sum_{i \in A_k} w_i.$$

The solution to the equation $$\min_{A_k \in K_U} \sum_{i \in A_k} w_i$$

in the subproblem can be solved by the following steps. The minimization in the equation $$\min_{A_k \in K_U} \sum_{i \in A_k} w_i$$

can be realized row by row, i.e., for each row of MLC leaf positions finding a consecutive set of beamlets for which the sum of their $w_i$ values is minimized. This can be achieved by passing through all beamlets in each row from left to right only once. The previous two steps can result in a set of consecutive beamlets in each MLC row at all un-occupied beam angles. These MLC rows can be grouped at each angle as an aperture. The deliverability of the solution aperture $A_k$ can be ensured by checking the left and right MLC leaf positions in each MLC row at the neighboring occupied beam angles. The aperture can be picked at one of the unoccupied beam angles which gives the minimal or smallest objective values, or which decreases the objective value most, as the final solution to this subproblem.

As for the master problem, the objective function can be of a quadratic form given the apertures $A_k$ have been determined in previous steps. Therefore, the master problem can be solved using gradient-based, interior point, or sequential quadratic methods to solve the nonlinear convex optimization problem, for example.

Figure 1A:
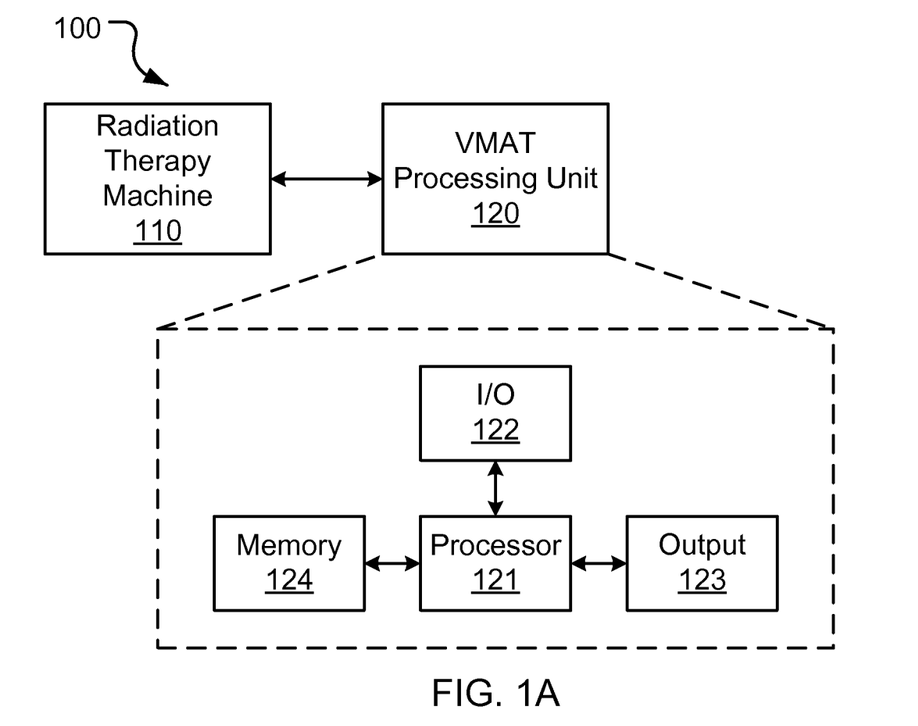
FIG. 1A is an exemplary system illustrating a radiation treatment device performing an optimized VMAT treatment plan.

FIG. 1A shows an exemplary radiation treatment system 100 for providing volume modulated arc therapy to a patient using a VMAT treatment process. FIG. 1A shows one aspect of the exemplary radiation treatment system 100 that may include a radiation therapy machine 110 that can be controlled by a VMAT processing unit 120.

The exemplary radiation therapy machine 110 can be used for curative or adjuvant treatment plans through the emission of ionizing radiation targeted at abnormal cells, such as diseased cells or cancer cells. The radiation therapy machine 110 can be used in the system 100 to implement a VMAT treatment optimization process under the control of the exemplary VMAT processing unit 120. The radiation therapy machine 110 can include various types of radiation therapy systems, such as an external beam radiotherapy machine (2DXRT), stereotactic radiation machine (SRS), virtual simulation 3-dimensional conformal radiotherapy machine (3DCRT), virtual simulation IMRT machine, and particle therapy and proton therapy machines.

The exemplary VMAT processing unit 120 can include a processor 121 that can be in communication with an input/output (I/O) unit 122, an output unit 123, and a memory unit 124. The VMAT processing unit 120 can be implemented as one of various data processing systems, such as a personal computer (PC), laptop, and mobile communication device. To support various functions of the VMAT processing unit 120, the exemplary processor 121 can be included to interface with and control operations of other components of the VMAT processing unit 120, such as the exemplary I/O unit 122, the exemplary output unit 123, and the exemplary memory unit 124.

To support various functions of the VMAT processing unit 120, the memory unit 124 can store other information and data, such as instructions, software, values, images, and other data processed or referenced by the processor 121. Various types of Random Access Memory (RAM) devices, Read Only Memory (ROM) devices, Flash Memory devices, and other suitable storage media can be used to implement storage functions of the memory unit 124. The memory unit 124 can store radiation therapy data and information, which can include patient diagnostic data, patient CT image data, dosimetry data, prescription data, radiation therapy machine system parameters, and MLC hardware constraints, which can be used in the implementation of a VMAT treatment plan. The memory unit 124 can store data and information that can be used to implement a VMAT treatment plan and that can be generated from a VMAT treatment plan.

To support various functions of the VMAT processing unit 120, the I/O unit 122 can be connected to an external interface, source of data storage, or display device. Various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement the I/O unit 122. The I/O unit 122 can interface with an external interface, source of data storage, or display device to retrieve and transfer data and information that can be processed by the processor 121, stored in the memory unit 124, or exhibited on the output unit 123.

To support various functions of the VMAT processing unit 120, the output unit 123 can be used to exhibit data implemented by the exemplary VMAT processing unit 120. The output unit 123 can include various types of display, speaker, or printing interfaces to implement the exemplary output unit 123. For example, the output unit 123 can include cathode ray tube (CRT), light emitting diode (LED), or liquid crystal display (LCD) monitor or screen as a visual display to implement the output unit 123. In other examples, the output unit 123 can include toner, liquid inkjet, solid ink, dye sublimation, inkless (such as thermal or UV) printing apparatuses to implement the output unit 123; the output unit 123 can include various types of audio signal transducer apparatuses to implement the output unit 123. The output unit 123 can exhibit data and information, such as patient diagnostic data, radiation therapy machine system information, a partially processed VMAT treatment plan, and a completely processed VMAT treatment plan. The output unit 123 can store data and information used to implement a VMAT treatment plan and from an implemented VMAT treatment plan.

Figure 1B:
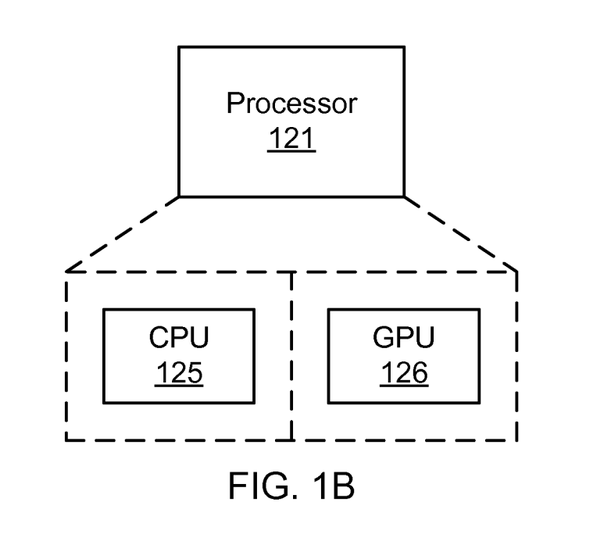
FIG. 1B is an exemplary processor that can include a CPU and a GPU.

FIG. 1B shows another aspect of the exemplary processor 121 that may include a CPU 125 or a GPU 126, or both a CPU 125 and a GPU 126. The exemplary CPU 125 and GPU 126 can interface with and control operations of other components of the VMAT processing unit 120, such as the I/O unit 122, the output unit 123, and the memory unit 124.

The exemplary process illustrated in FIG. 1A is described with respect to exemplary process flow diagrams in FIGS. 2A, 2B, 2C, 2D, and 2E.

Figure 2A:
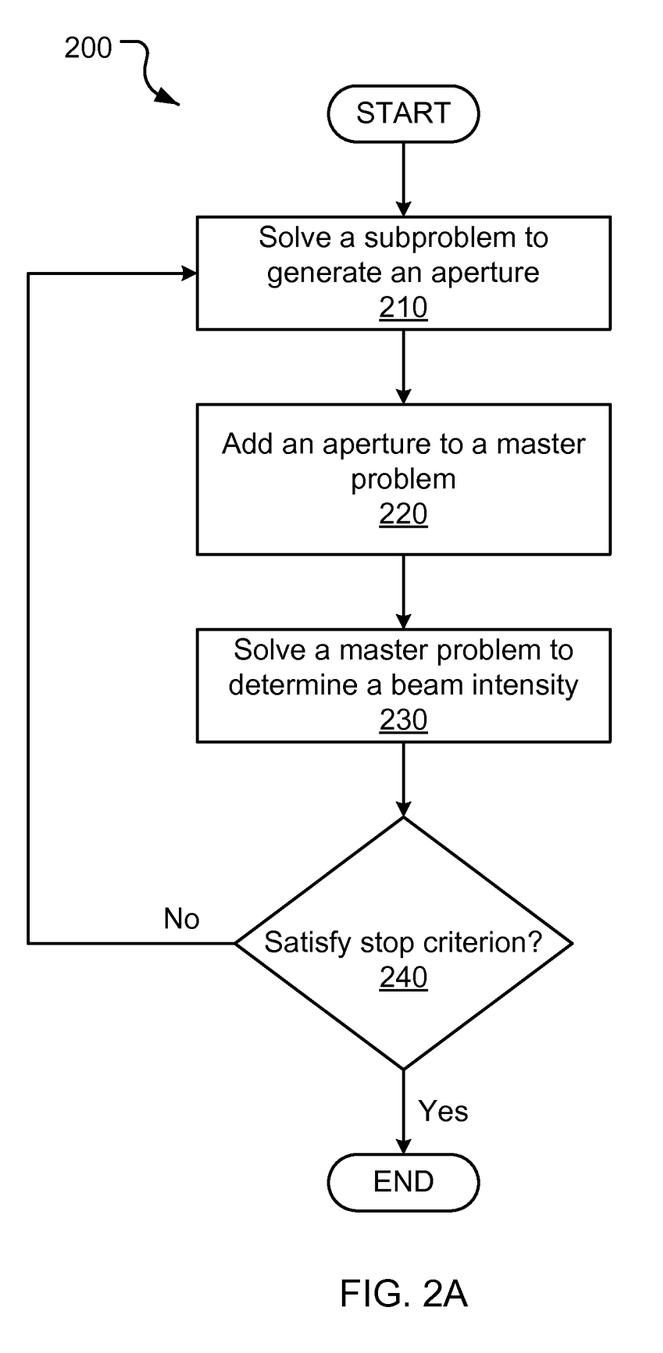
FIG. 2A is a flow diagram showing an exemplary process to implement a VMAT treatment plan optimization problem.

The flow diagram of the exemplary process 200 to optimize a VMAT treatment plan using a column generation approach is summarized in FIG. 2A. A system (e.g., system 100) can perform the process 200 as described and illustrated in FIG. 2A. The system can solve the subproblem to generate a deliverable aperture at an unoccupied beam angle (process 210). For example, the process 210 can be solved using a polynomial-time process. The system can add the deliverable aperture generated by the subproblem to the master problem (process 220). The system can solve the master problem to determine the associated beam intensity (process 230). For example, the process 230 can be solved using a gradient-based process. The system can repeat processes 210, 220, and 230 to generate another deliverable aperture as long as there remain beam angles unoccupied by a deliverable aperture (240—No). Otherwise the stop criterion is satisfied (240—Yes), and the system can terminate the process 200.

Figure 2B:
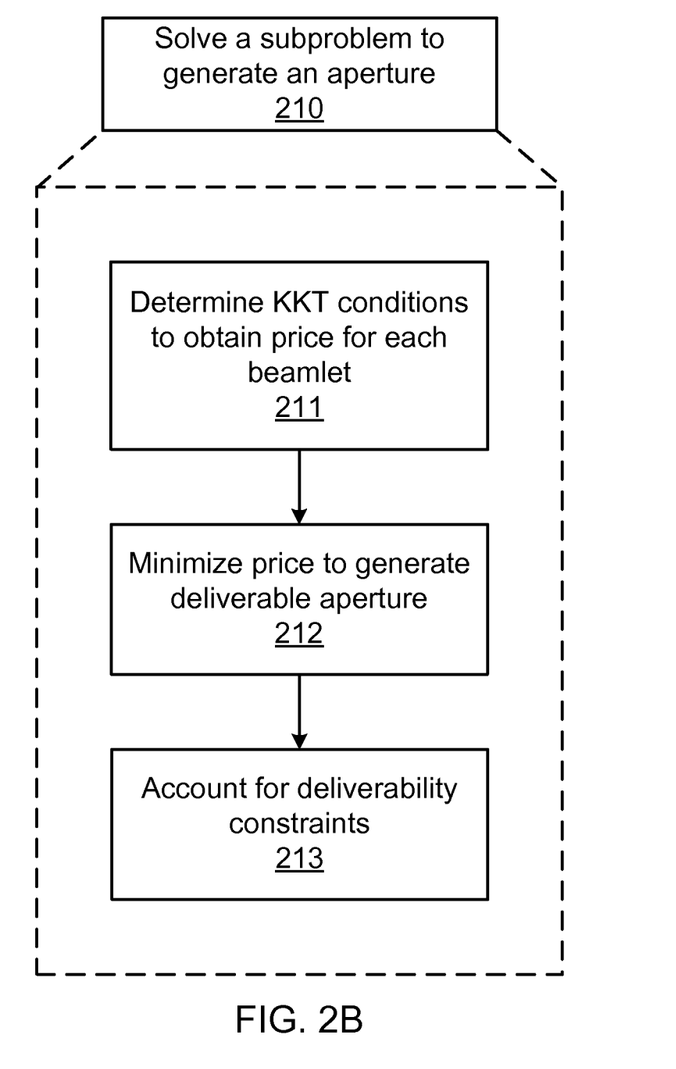
FIG. 2B is a block diagram showing an exemplary process to solve a subproblem to generate an aperture.

FIG. 2B is a block diagram showing an exemplary process 210 to solve the subproblem to generate a deliverable aperture at an unoccupied beam angle. A system (e.g., system 100) can perform the process 210 as described and illustrated in FIG. 2B. The system can perform a process that can determine the Karush-Kuhn-Tucker (KKT) conditions to obtain the price for each beamlet (211). The system can perform a process that can minimize the price value of each beamlet to generate the deliverable aperture with the minimal or smallest objective value (212). The system can perform a process that can account for deliverability constraints to ensure the deliverability of the solution aperture to the master problem (213).

Figure 2C:
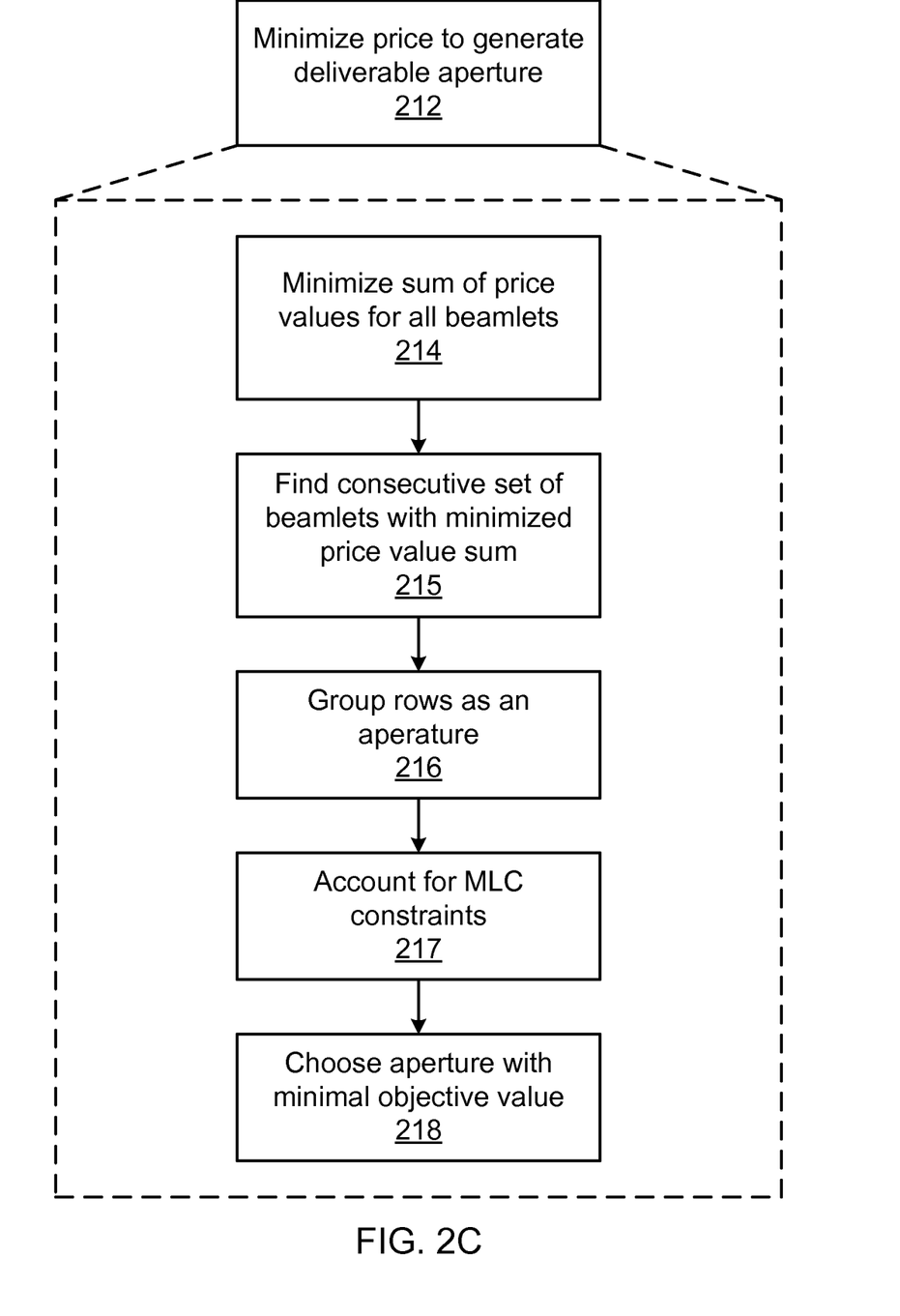
FIG. 2C is a block diagram showing an exemplary process to minimize the price to generate an aperture in the exemplary subproblem.

FIG. 2C is a block diagram showing an exemplary process 212 to minimize the price in the exemplary process 210 to solve the subproblem. A system (e.g., system 100) can perform the process 212 as described and illustrated in FIG. 2C. The system can perform a process that can minimize the sum of price values for all beamlets for each MLC row by passing through all beamlets in each row from left to right once (214). The system can perform a process that can find a consecutive set of beamlets for which the sum of their price values is minimized for each MLC row by passing through all beamlets in each row from left to right once (215). The system can perform a process that can group the MLC rows of consecutive sets of beamlets with minimized price value sums (216). The system can perform a process that can account for MLC leaf position, speed, and other hardware constraints (217). The system can perform a process that can choose the aperture with the minimal or smallest objective value (218).

Figure 2D:
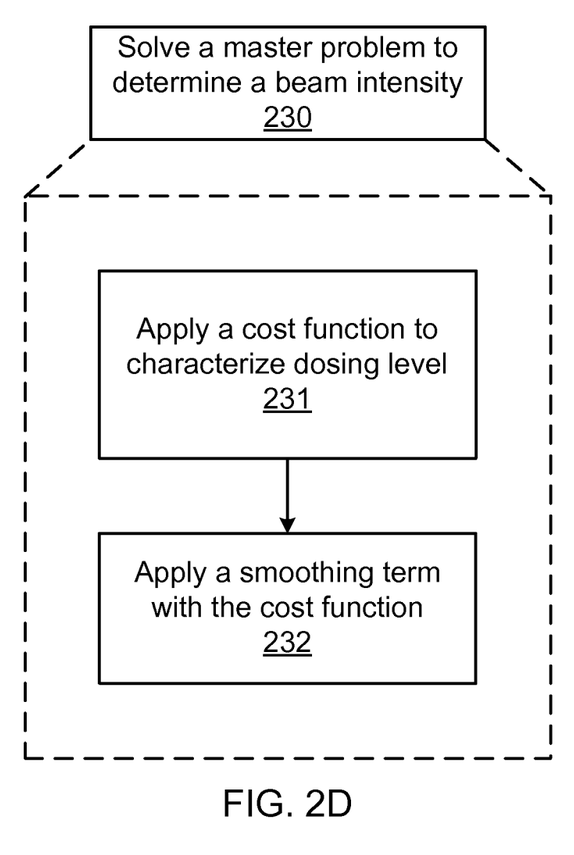
FIG. 2D is a block diagram showing an exemplary process to solve a master problem to determine a beam intensity.

FIG. 2D is a block diagram showing an exemplary process 230 to solve the master problem to determine the beam intensity of an added deliverable aperture. A system (e.g., system 100) can perform the process 230 as described and illustrated in FIG. 2D. The system can perform a process that can apply a cost function to characterize and mitigate the dosing level, such as an underdose, overdose, and the prescribed dose amount (231). The system can perform a process that can apply a smoothing term to minimize differences between beam intensities at neighboring beam angles (232).

Figure 2E:
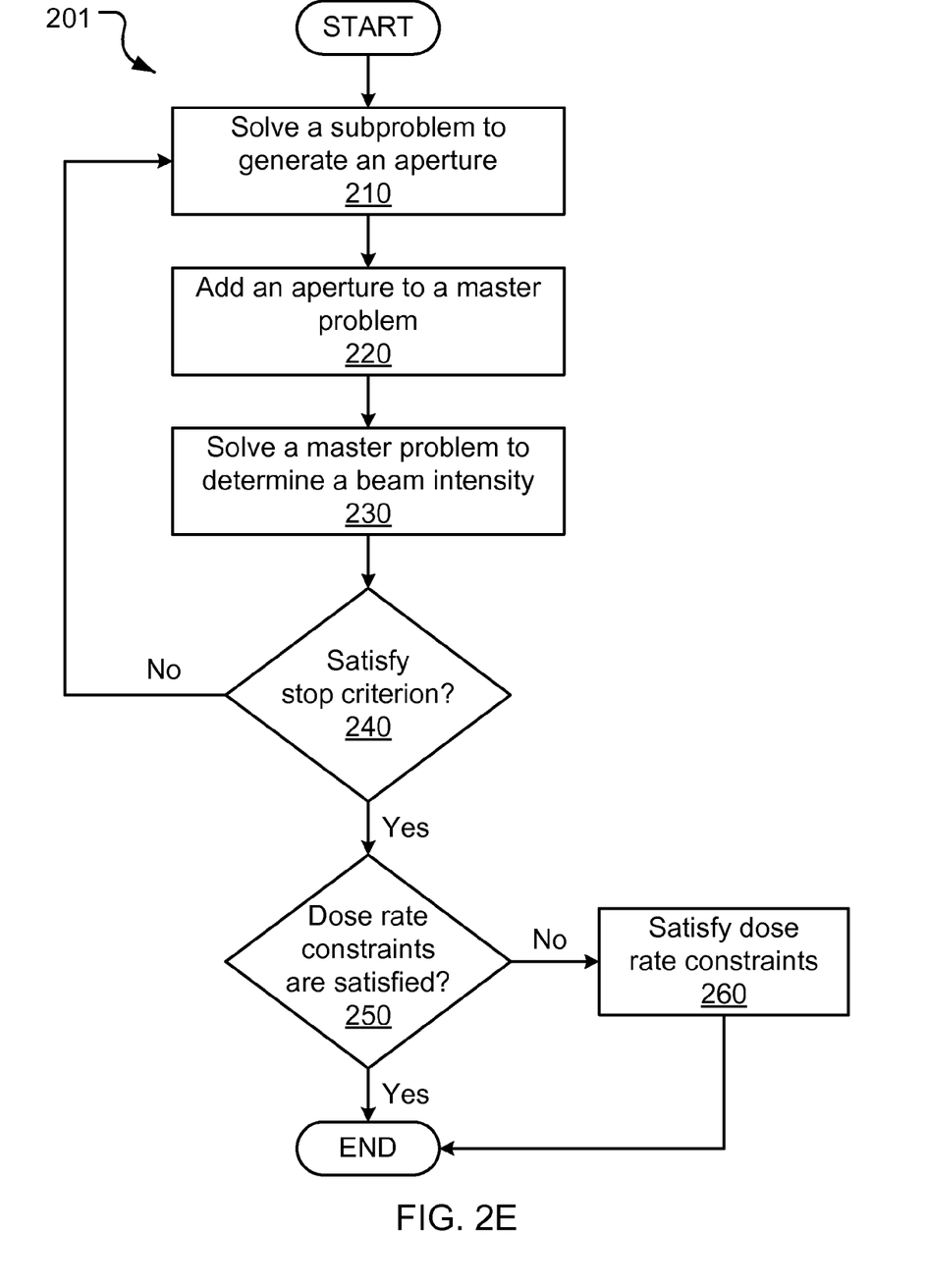
FIG. 2E is a flow diagram showing another exemplary process to implement a VMAT treatment plan optimization problem.

The flow diagram of another exemplary process 201 to optimize a VMAT treatment plan using a column generation approach is summarized in FIG. 2E. A system (e.g., system 100) can perform the process 201 as described and illustrated in FIG. 2E. The system can solve the subproblem to generate a deliverable aperture at an unoccupied beam angle (process 210). For example, the process 210 can be solved using a polynomial-time process. The system can add the deliverable aperture generated by the subproblem to the master problem (process 220). The system can solve the master problem to determine the associated beam intensity (process 230). For example, the process 230 can be solved using a gradient-based process. The system can repeat processes 210, 220, and 230 to generate another deliverable aperture as long as there remain beam angles unoccupied by a deliverable aperture (240—No). Otherwise the stop criterion is satisfied (240—Yes), and the system can check the dose rate constraints are satisfied. If the dose rate constraints are not satisfied (250—No), the system can satisfy the dose rate constraints by adjusting a relative weight coefficient between the cost function and the smoothing term (process 260) and can terminate the process 201. If the dose rate constraints are satisfied (250—Yes), the system can terminate the process 201.

Experimental Results

In one implementation of the process, five clinical prostate cases (P1-P5) and five clinical head-and-neck cases (H1-H5) were used to evaluate the VMAT optimization process in terms of treatment plan quality and planning efficiency. For prostate cases, the prescription dose to planning target volume (PTV) was 73.8 Gy. For the head-and-neck cases, the prescription dose was 73.8 Gy to PTV1 and 54 Gy to PTV2. PTV1 can include the gross tumor volume (GTV) expanded to account for sub-clinical disease, as well as daily setup errors and internal organ motion. PTV2 is a larger target that can include high-risk nodal regions and is also expanded. For these exemplary cases, a beamlet size of 10×10 mm$^2$ and voxel size of 2.5×2.5×2.5 mm$^3$ was used for target and organs at risk (OARs). For unspecified tissue (i.e., tissues outside the target and OARs), the voxel size in each dimension was increased by a factor of 2 to reduce the optimization problem size. The full resolution was used when evaluating the treatment quality via DVHs, dose color wash, isodose curves, etc.

Figure 3A:
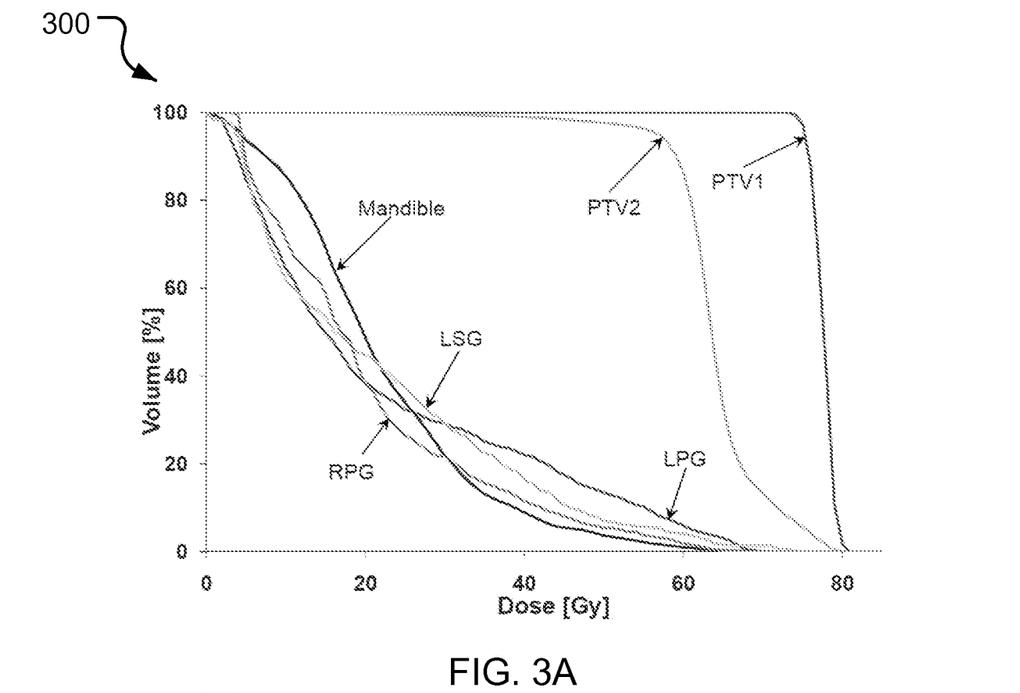
FIG. 3A shows an exemplary dose volume histogram (DVH) resulting from an implementation of the VMAT treatment plan for a head-and-neck clinical case.
Figure 3B:
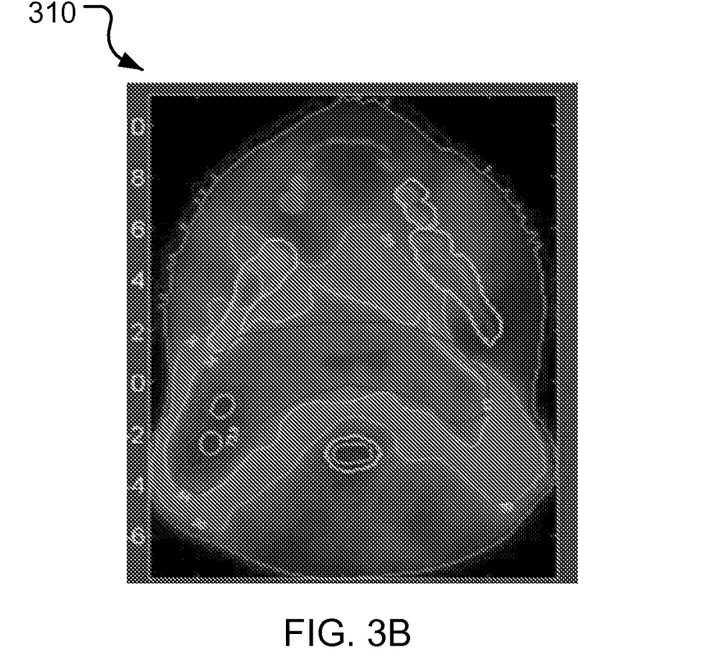
FIG. 3B shows an exemplary isodose/dose wash superimposed on the representative computed tomography (CT) slice from a head-and-neck clinical case.
Figure 4A:
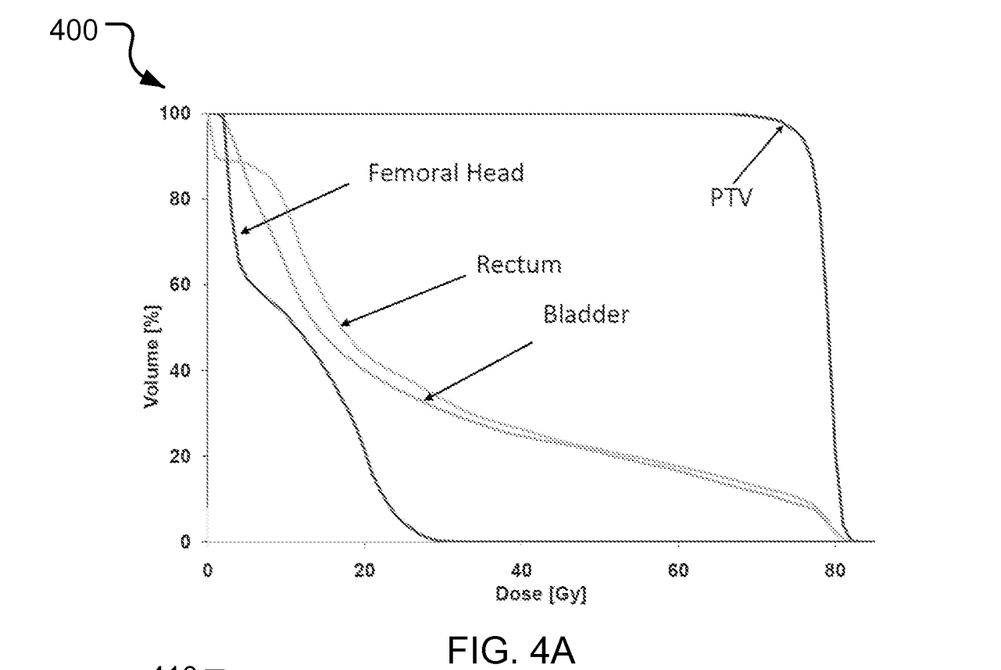
FIG. 4A shows an exemplary DVH resulting from an implementation of the VMAT treatment plan for a prostate clinical case.
Figure 4B:
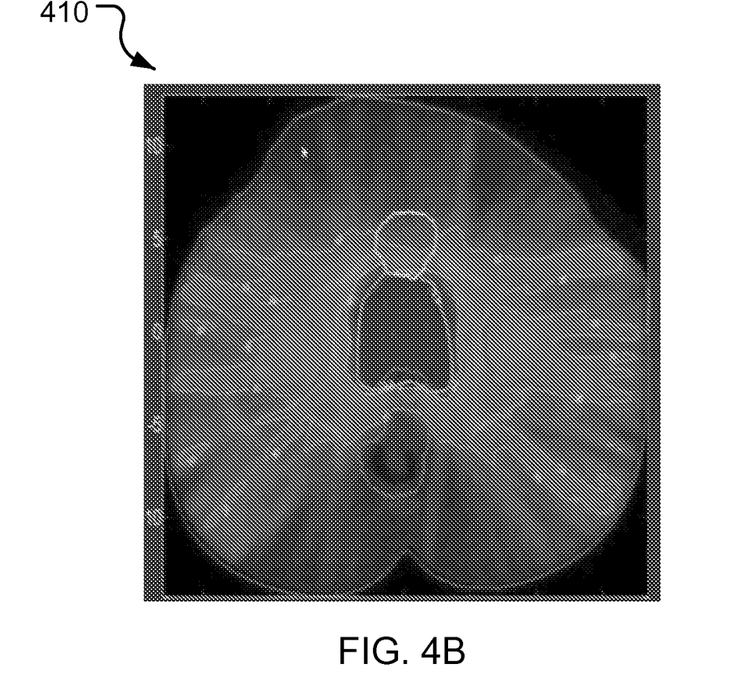
FIG. 4B shows an exemplary isodose/dose wash superimposed on the representative CT slice from a prostate clinical case.

Two exemplary VMAT plans are shown in FIGS. 3A and 3B for an exemplary head-and-neck case and in FIGS. 4A and 4B for an exemplary prostate case. By solving the VMAT optimization problem, the shape of an aperture and its associated beam intensity can be obtained, by which the dose given to each voxel can be determined and a process for a VMAT treatment plan is optimized. FIG. 3A shows a plot 300 of the DVH of an exemplary VMAT treatment plan for the exemplary head-and-neck case; FIG. 3B shows a plot 310 of isodose/dose wash superimposed on the representative CT slice for an exemplary VMAT treatment plan for the exemplary head-and-neck case. The exemplary plot 300 in FIG. 3A includes the DVH curves of the left submandibular gland (LSG), left parotid gland (LPG), right parotid gland (RPG), and mandible structures, as well as prescription dose to planning target volume curves of PTV1 and PTV2 for this exemplary clinical head-and-neck case. FIG. 4A shows a plot 400 of the DVH of an exemplary VMAT treatment plan for the exemplary prostate case; FIG. 4B shows a plot 410 of isodose/dose wash superimposed on the representative CT slice for the exemplary VMAT treatment plan for the exemplary prostate case. The exemplary plot 400 in FIG. 4A includes the DVH curves of the femoral head, rectum, and bladder structures, as well as prescription dose to planning target volume curve PTV for this exemplary clinical prostate case.

The dimensions of the exemplary cases are displayed in Table 1. For each of the exemplary cases shown in Table 1, case dimensions that include the number of beamlets, voxels, and non-zero $D_{ij}$ values were processed on a CPU and GPU system, e.g., an Intel Xeon 2.27 GHz CPU and an NVIDIA Tesla C1060 GPU. The CPU and GPU running times are comparatively shown for exemplary VMAT plan optimization implementations.

| Case | Number of beamlets | Number of voxels | Number of non-zero $D_{ij}$'s (×10$^7$) | CPU time (sec) | GPU time (sec) | Number of beamlets |
|---|---|---|---|---|---|---|
| P1 | 40,620 | 45,912 | 2.3 | 340 | 22 | 40,620 |
| P2 | 59,400 | 48,642 | 3.2 | 265 | 18 | 59,400 |
| P3 | 38,880 | 28,931 | 1.8 | 276 | 20 | 38,880 |
| P4 | 43,360 | 39,822 | 2.6 | 410 | 26 | 43,360 |
| P5 | 51,840 | 49,210 | 3.0 | 348 | 23 | 51,840 |
| H1 | 51,709 | 33,252 | 2.5 | 290 | 21 | 51,709 |
| H2 | 78,874 | 59,615 | 5.0 | 468 | 27 | 78,874 |
| H3 | 90,978 | 74,438 | 5.5 | 342 | 25 | 90,978 |
| H4 | 71,280 | 31,563 | 2.6 | 363 | 25 | 71,280 |
| H5 | 53,776 | 42,330 | 3.5 | 512 | 31 | 53,776 |

As seen in Table 1, the VMAT optimization process has very high planning efficiency. A high quality treatment plan was generated in the exemplary implementation in only 5 to 8 minutes on an Intel Xeon 2.27 GHz CPU and in only 18 to 31 seconds with the computer unified device architecture (CUDA) implementation on an NVIDIA Tesla C1060 GPU card. The experimental results shown in Table 1 can be used to validate VMAT as a treatment delivery technique for online adaptive radiation therapy.

The shape of an aperture does not change once it is generated, while the intensity of this aperture can still be adjustable at each iteration by solving the master problem. It was found that after generating one aperture for each beam angle using the described method, adding more apertures to a beam angle did not significantly improve the quality of a VMAT plan. This can be attributed to a large number of beam angles used (such as 180 angles, as in the exemplary implementation) and the contribution of each individual beam angle is relatively small.

Although the dose rate constraints can be formulated as penalty-based soft constraints in the cost function, the dose rate constraints should be satisfied at the end of the optimization. For example, the dose rate constraints can be satisfied at the last iteration after generating the last aperture. The coefficient $\gamma$ in the objective function can be automatically increased if the dose rate constraints are not satisfied at the last iteration, and then the intensity for each aperture can be re-optimized until the dose rate constraints are satisfied. A similar approach can also be used to handle the maximum and minimum dose rate constraints.

Implementations of the subject matter and the functional operations described in this specification can be implemented in systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

What is claimed is:

1. A method performed by an aperture-based radiation treatment system to implement a volumetric modulated arc therapy (VMAT), the method comprising:
    generating apertures at beam angles;
    determining beam intensities of the generated apertures, wherein the determining the beam intensities comprises minimizing the difference between beam intensities at two neighboring beam angles; and
    using the determined beam intensities of the generated apertures to control generation of radiation dose in a radiation therapy.

2. The method of claim 1, wherein determining the beam intensities comprises:
    determining beam intensity for a given aperture generated based on beam intensities for previously generated apertures.

3. The method of claim 1, wherein the beam angles are user defined for a rotation.

4. The method of claim 1, wherein the beam angles are uniformly spaced for a rotation.

5. The method of claim 1, wherein generating the apertures comprises:
    using a column generation method.

6. The method of claim 1, wherein generating the apertures and determining the beam intensities are performed in an iterative process.

7. The method of claim 1, wherein a given aperture is generated with the minimal objective value.

8. The method of claim 1, wherein determining the aperture shapes and beam intensities comprises:
    using a cost function to characterize a quality of the radiation therapy.

9. The method of claim 8, wherein the quality of the radiation therapy comprises a level of the radiation dose.

10. The method of claim 1, wherein the apertures are generated incorporating constraints for delivering the radiation dose.

11. A system for radiation treatment using a volumetric modulated arc therapy (VMAT), the system comprising:
  a VMAT processing unit configured to perform the following:
    generating apertures at beam angles, and
    determining beam intensities of the generated apertures, wherein the VMAT processing unit is configured to determine the beam intensities including by minimizing the difference between beam intensities at two neighboring beam angles; and
  a radiation therapy device configured to use the determined beam intensities of the generated apertures to control generation of radiation dose in a radiation therapy.

12. The system of claim 11, wherein the VMAT processing unit comprises a graphics processing unit.

13. The system of claim 11, wherein the VMAT processing unit comprises a central processing unit.

14. The system of claim 11, wherein the VMAT processing unit is configured to determine the beam intensities comprising:
  determining beam intensity for a given aperture generated based on beam intensities for previously generated apertures.

15. The system of claim 11, wherein the VMAT processing unit is configured to determine the aperture shapes and beam intensities comprising:
  using a cost function to characterize a level of the radiation dose.

16. The system of claim 11, wherein the VMAT processing unit is configured to generate a given aperture incorporating constraints for delivering the radiation dose.

17. A non-transient computer-readable medium embodying a computer program product adapted to cause a system to perform radiation treatment operations using a volumetric modulated arc therapy (VMAT), the operations comprising:
  generating apertures at beam angles; and
  determining beam intensities of the generated apertures, wherein the determining the beam intensities comprises minimizing the difference between beam intensities at two neighboring beam angles; and
  using the determined beam intensities of the generated apertures to control generation of radiation dose in a radiation therapy.

18. The non-transient computer-readable medium of claim 17, wherein the operations comprise:
  determining beam intensity for a given aperture generated based on beam intensities for previously generated apertures.

19. The non-transient computer-readable medium of claim 17, wherein the operations comprise:
  determining the aperture shapes and beam intensities comprises using a cost function to characterize a level of the radiation dose.

20. The non-transient computer-readable medium of claim 17, wherein the operations comprise:
  generating the apertures comprises incorporating constraints for delivering the radiation dose.

* * * * *